(12) United States Patent
Virk et al.

(10) Patent No.: US 9,622,984 B1
(45) Date of Patent: Apr. 18, 2017

(54) SYNTHESIS OF NARINGENIN NANOPARTICLES

(71) Applicant: KING SAUD UNIVERSITY, Riyadh (SA)

(72) Inventors: Promy Virk, Riyadh (SA); Nouf Abdallah Mureet Al-Ghamdi, Riyadh (SA); Manal Ahmed Gasmelseed Awad, Riyadh (SA); Mai Abdelrahman Elobeid Wagealla, Riyadh (SA); Awatif Ahmed Hendi, Riyadh (SA); Lulwah Saleh Mohammed Al Hassan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/141,781

(22) Filed: Apr. 28, 2016

(51) Int. Cl.
*A61K 9/51* (2006.01)
*A61K 31/353* (2006.01)

(52) U.S. Cl.
CPC .......... *A61K 9/5192* (2013.01); *A61K 31/353* (2013.01)

(58) Field of Classification Search
CPC ............................ A61K 9/5192; A61K 31/353
See application file for complete search history.

(56) References Cited

U.S. PATENT DOCUMENTS 6,165,984 A 12/2000 Bok et al.

OTHER PUBLICATIONS

Löf, D., "Flavonoids: precipitation kinetics and interaction with surfactant micelles." Journal of food science 76.3 (2011): N35-N39.*
Yen, F-L.,"Naringenin-loaded nanoparticles improve the physicochemical properties and the hepatoprotective effects of naringenin in orally-administered rats with CCl4-induced acute liver failure." Pharmaceutical research 26.4 (2009): 893-902.*
Yen et al., "Naringenin-Loaded Nanoparticles Improve the Physicochemical Properties and the Hepatoprotective Effects of Naringenin in Orally-Administered Rats with $CCl_4$-Induced Acute Liver Failure," *Pharmaceutical Research*, Apr. 2009, 200, vol. 26, pp. 893-902.

* cited by examiner

*Primary Examiner* — Samantha Shterengarts
*Assistant Examiner* — Matt Mauro
(74) *Attorney, Agent, or Firm* — Richard C. Litman

(57) ABSTRACT

A method of preparing naringenin nanoparticles comprises dissolving naringenin in an organic solvent to form a solution; adding the solution to boiling water under ultrasonic conditions to form a mixture; and stirring the mixture to obtain the naringenin nanoparticles. The organic solvent can be at least one of methanol, ethanol, dichloromethane and chloroform. Ultrasonic conditions can include applying ultrasonic energy at a frequency of 30-60 kHz and a power of 100 watts for about 20-30 minutes to the mixture.

10 Claims, 10 Drawing Sheets

SYNTHESIS OF NARINGENIN NANOPARTICLES

BACKGROUND OF THE INVENTION

1. Field of the Invention

The present invention relates to bio-nanotechnology and particularly to a method of synthesizing naringenin nanoparticles for safe antioxidant therapy.

2. Description of the Related Art

Cadmium (Cd) is a non-essential toxic heavy metal and can be found at elevated levels in water and sediments of the aquatic environment as a result of natural and anthropogenic activities. Cadmium-related contamination of the aquatic habitat has greatly increased in the last decades, resulting in an increase of cadmium deposits in tissues of aquatic organisms. It has been found that accumulation of heavy metals including Cd in fish can trigger the production of reactive oxygen species (ROS) such as superoxide anion radical, hydrogen peroxide, hydroxyl radical, singlet oxygen, lipid hydroperoxide and alkoxyl radical. These ROS react with susceptible biological macromolecules, resulting in lipid peroxidation (LPO) and antioxidant defense alterations, a condition best described as oxidative stress.

At biochemical levels, lipid peroxidation and enzyme antioxidant systems have great potential to indicate cellular responses to the toxic effects of Cd, and have been widely studied in fish as biomarkers of metal induced oxidative stress. The induction of metallothionein (MT) together with the antioxidant enzymes is considered to play a protective role against Cd oxidative stress and is one of the most widely studied effects of Cd exposure. Besides the more frequently studied biomarkers of metal-induced-stress in fish, another protection system is represented by the heat shock protein 70 (HSP70). It is believed that the induction of HSP70 is an evolutionary conserved response of the organisms towards exposure to pro-oxidants.

Chelation, antioxidant and herbal therapies are three strategies commonly used for treatment of metal toxicity. Owing to the intrinsic limitations and variability of efficacy of chelating agents, however, antioxidants, and naturally occurring antioxidants in particular, are more desirable for cadmium toxicity therapy. Flavonoids represent an example of one of the most numerous and widespread group of naturally occurring antioxidants that can inhibit lipid oxidation in a biological membrane. Naringenin (4,5,7-trihydroxyflavanone), for example, is a natural flavonoid, a glycone of naringin, and a well-documented antioxidant compound.

Thus, a method of producing eco-friendly non-metal naringenin nanoparticles solving the aforementioned problems is desired.

SUMMARY OF THE INVENTION

A method of preparing naringenin nanoparticles comprises dissolving naringenin in an organic solvent to form a solution; adding the solution to boiling water under ultrasonic conditions to form a mixture; and stirring the mixture to obtain the naringenin nanoparticles. The organic solvent can be at least one of methanol, ethanol, dichloromethane and chloroform. Ultrasonic conditions can include applying ultrasonic energy at a frequency of 30-60 kHz and a power of 100 watts for about 20-30 minutes to the mixture.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

A method for preparing naringenin nanoparticles is provided. The naringenin nanoparticles can be non-metal nanoparticles. The method of preparing naringenin nanoparticles comprises dissolving naringenin, i.e. bulk naringenin, in an organic solvent to form a solution; adding the solution to boiling water under ultrasonic conditions to form a mixture; and stirring the mixture to obtain the naringenin nanoparticles.

The nanoparticle solution can be added to, e.g., sprayed into, the boiling water dropwise with a flow rate of about 0.2 mL/min for 5 minutes. The ultrasonic conditions can include ultrasonically irradiating the mixture with a power of 100 W and a frequency of 30-60 $kH_z$ for a period of about 20 to about 30 minutes. The mixture can be stirred for about 15 to about 30 minutes at 30° C. to about 50° C. The naringenin nanoparticles can be isolated by conventional methods, such as centrifugation and/or filtration. The organic solvent can include at least one of methanol, ethanol, dichloromethane and chloroform. The naringenin nanoparticles prepared by the present technique display a mean diameter in the range of from about 50 nm to about 200 nm, and can have spherical, spheroidal, elongated spherical, rod-shaped, and/or faceted shapes.

Naringenin (4,5,7-trihydroxyflavanone) is a flavanone, considered to have a bioactive effect on human health as an antioxidant, free radical scavenger, anti-inflammatory, carbohydrate metabolism promoter, and immune system modulator. It is the predominant flavanone in grapefruit, oranges and lemons. Its chemical structure is depicted below:

Naringenin is a well-documented antioxidant compound and its bioactivity has been attributed to its structure-activity relationship. Despite the fact that naringenin has excellent free radical scavenging abilities, clinical studies exploring different regimens of administration of this compound have been hampered by its extreme water insolubility.

Relative to bulk naringenin, naringenin nanoparticles can be more adequately delivered to biological systems. Nanoparticle systems, generally, have proven highly promising in enhancing drug delivery. Nanoparticles have been successfully used to improve the physicochemical profiles of drug compounds and increase their bioavailability and solubility. Oxidative stress has been specifically implicated in metal toxicity and the pathogenesis of many chronic diseases, such as cancer, atherosclerosis, cardiovascular disease, and neurodegenerative disorders. Nanoparticle antioxidants constitute a new wave of antioxidant therapies for disease prevention and treatment in the field of oxidative stress.

The naringenin nanoparticles are non-metal nanoparticles that can be useful for treating oxidative stress, e.g., oxidative stress caused by accumulation of one more heavy metals in tissues of organisms, particularly aquatic organisms. The heavy metal can include cadmium (Cd), for example. The aquatic organisms can include freshwater and/or saltwater fish. An exemplary freshwater fish is the adult male Nile tilapia (Oreochromis niloticus). In addition, the naringenin nanoparticles can be useful as an antioxidant in the treatment of cancer. Naringenin nanoparticles can be effectively administered to an organism as a therapeutic agent for treating oxidative stress in an organism. Thus, a method of treating oxidative stress in an organism can include administering an effective amount of naringenin nanoparticles to the organism. The oxidative stress can be caused by cadmium accumulation in the organism or cancer.

As used herein, the term "Nanoparticle" refers to a particle having at least one dimension and sized between 1 and 100 nanometers. The nanoparticles can include naringenin nanoparticles. In some embodiments, the nanoparticles disclosed herein are from about 5 nm to about 500 nm in diameter, e.g., 100 to 200 nm. As used herein, the term "ultrasonication" refers to irradiation with ultrasonic (>20 kHz) waves. Ultrasonication may be performed using an ultrasonic bath or an ultrasonic probe.

The present technology, thus generally described, will be understood more readily by reference to the following examples, which is provided by way of illustration and is not intended to limit the scope of the present technology.

EXAMPLE 1

Synthesis of Naringenin Nanoparticles in Methanol

Figure 1A:
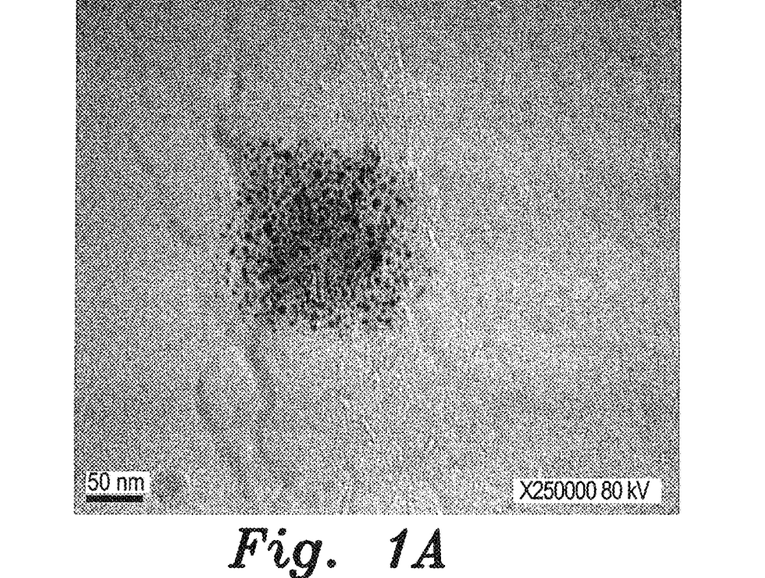
FIGS. 1A-1B show the transmission electron micrograph (TEM) images of the methanol-naringenin nanoparticles.
Figure 1B:
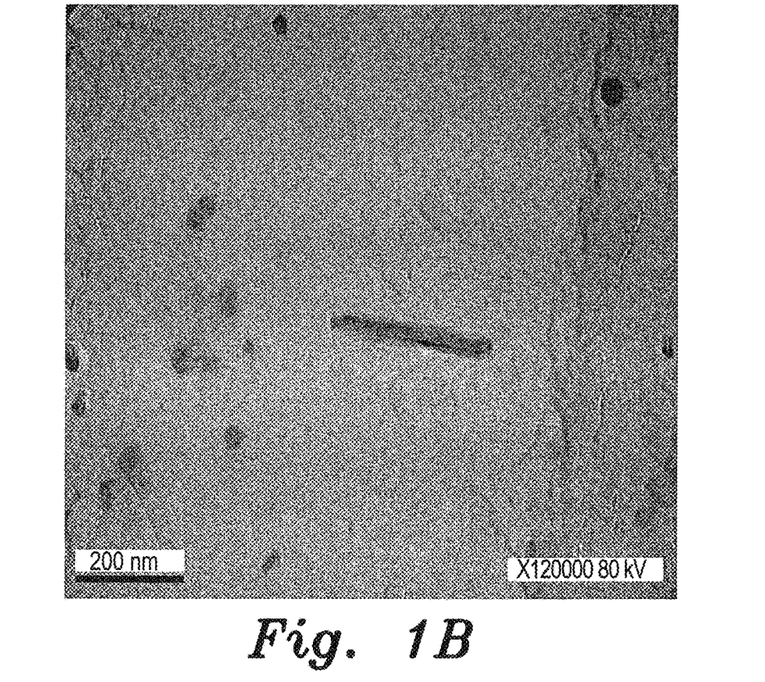
Figure 2:
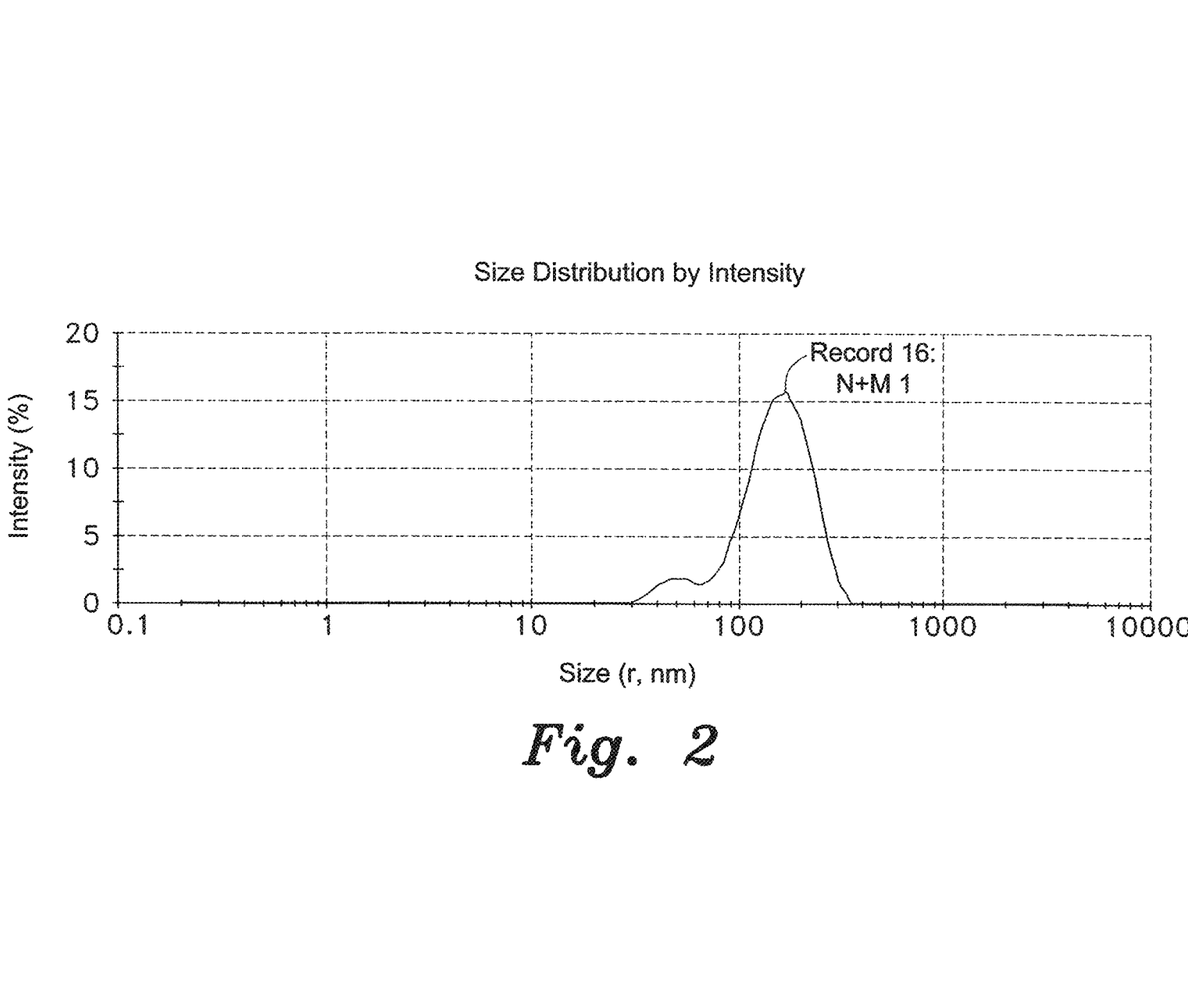
FIG. 2 is a graph showing the particle size distribution by intensity (Zetasizer) of the methanol-naringenin nanoparticles.

About 100 mg of naringenin powder was dissolved in about 20-50 ml methanol. The naringenin-methanol solution was sprayed into about 50-100 mL boiling water dropwise with a flow rate of 0.2 mL/min in 5 min under ultrasonic conditions, with an ultrasonic power of 100 W and a frequency of 30-60 kHz for 20-30 min. The solution was stirred for 15-30 min at 30-50° C. to obtain methanol-naringenin nanoparticles. FIGS. 1A and 1B show the transmission electron micrograph (TEM) images of the methanol-naringenin nanoparticles. The naringenin nanoparticles are spherical or rod shaped. FIG. 2 shows the naringenin particle size distribution by intensity (zetasizer) of the methanol-naringenin nanoparticles indicating the average particle size to be about 165 nm.

EXAMPLE 2

Synthesis of Naringenin Nanoparticles in Ethanol

Figure 3A:
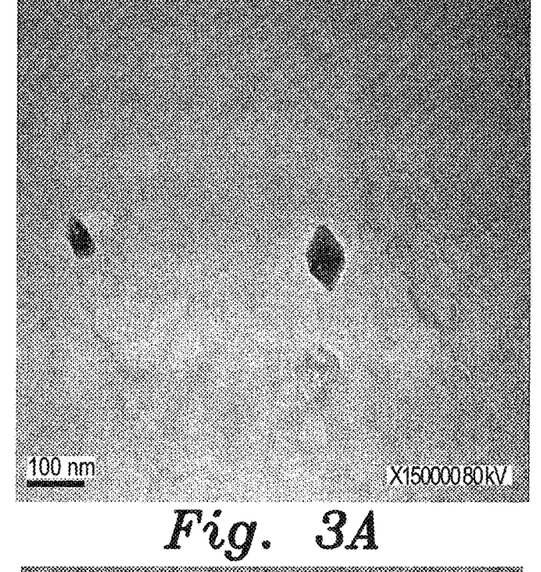
FIGS. 3A-3B-show the TEM images of the ethanol-naringenin nanoparticles.
Figure 3B:
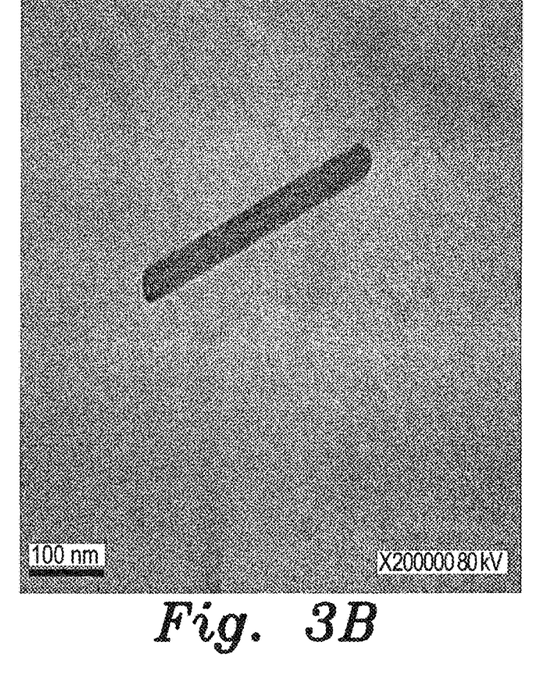
Figure 4:
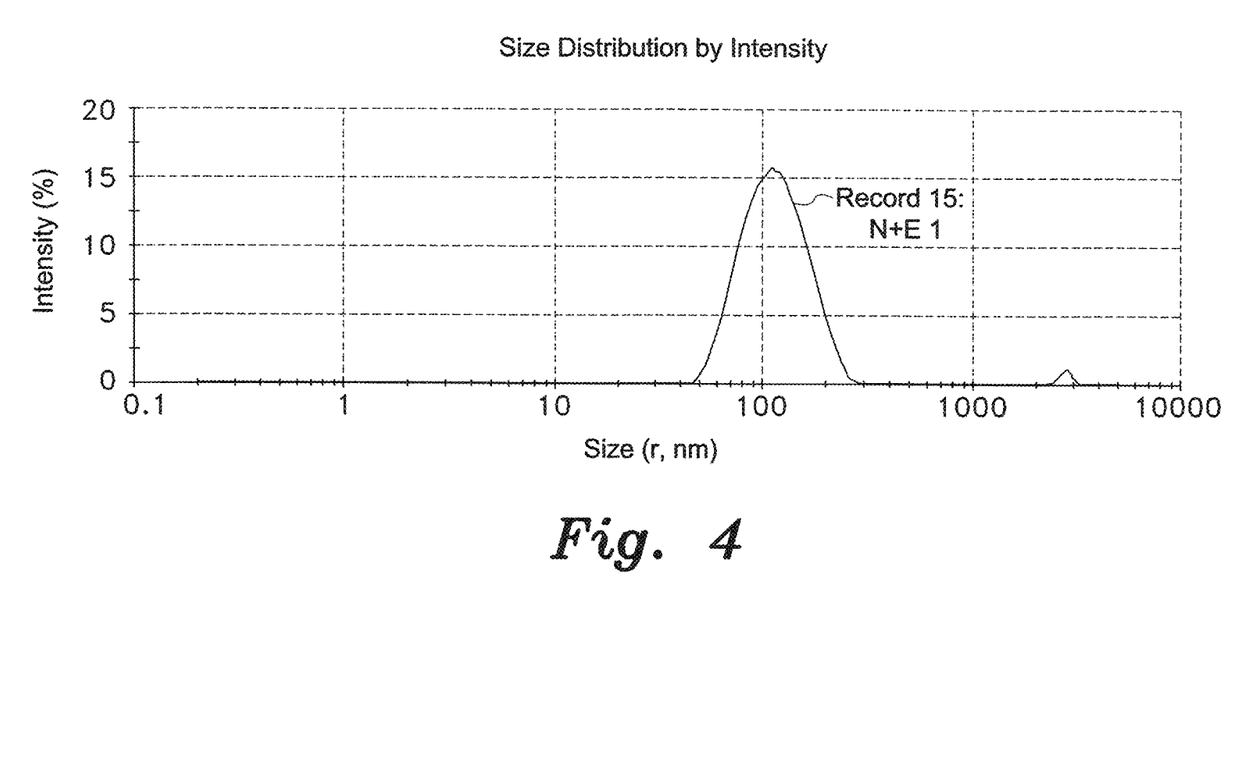
FIG. 4 is a graph showing the particle size distribution by intensity (Zetasizer) of the ethanol-naringenin nanoparticles.

About 100 mg of naringenin powder was dissolved in about 20-50 ml ethanol. The naringenin-ethanol solution was sprayed into about 50-100 mL boiling water dropwise with a flow rate of 0.2 mL/min in 5 min under ultrasonic conditions, with an ultrasonic power of 100 W and a frequency of 30-60 kHz for 20-30 min. The solution was stirred for 15-30 min at 30-50° C. to obtain ethanol-naringenin nanoparticles. FIGS. 3A-3B show the TEM images of the ethanol naringenin nanoparticles as being show faceted and rod shaped naringenin nanoparticles. FIG. 4 shows the ethanol-naringenin particle size distribution by intensity (zetasizser) of the ethanol-naringenin nanoparticles, indicating the average particle size to be about 120 nm.

EXAMPLE 3

Synthesis of Naringenin Nanoparticles in Dichloromethane

Figure 5A:
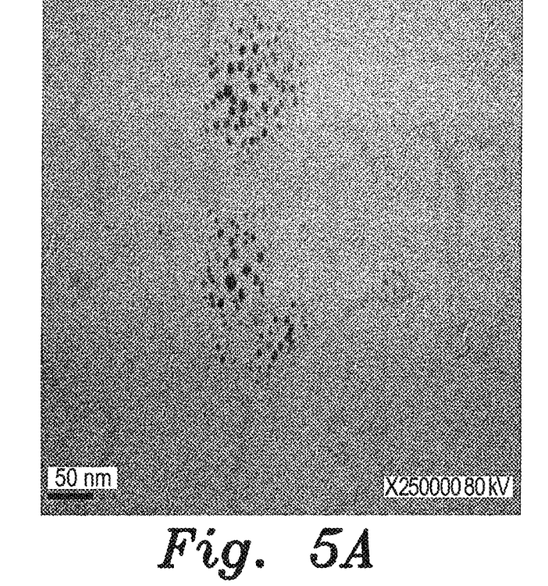
FIGS. 5A-5B is a graph showing the TEM images of the dichloromethane-naringenin nanoparticles.
Figure 5B:
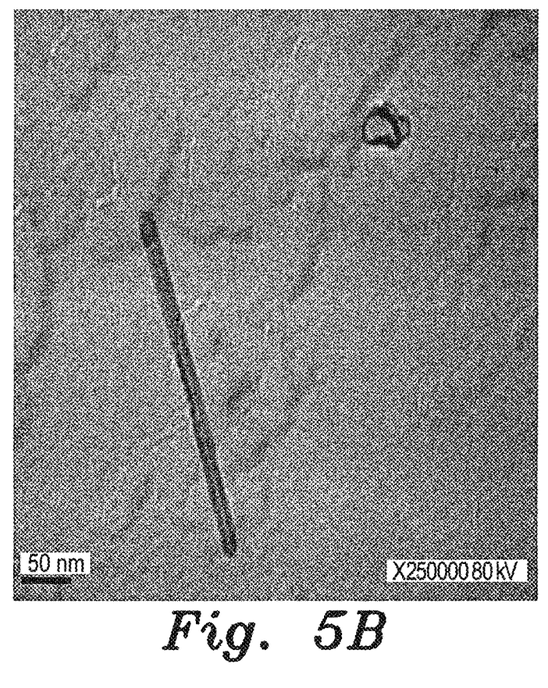
Figure 6:
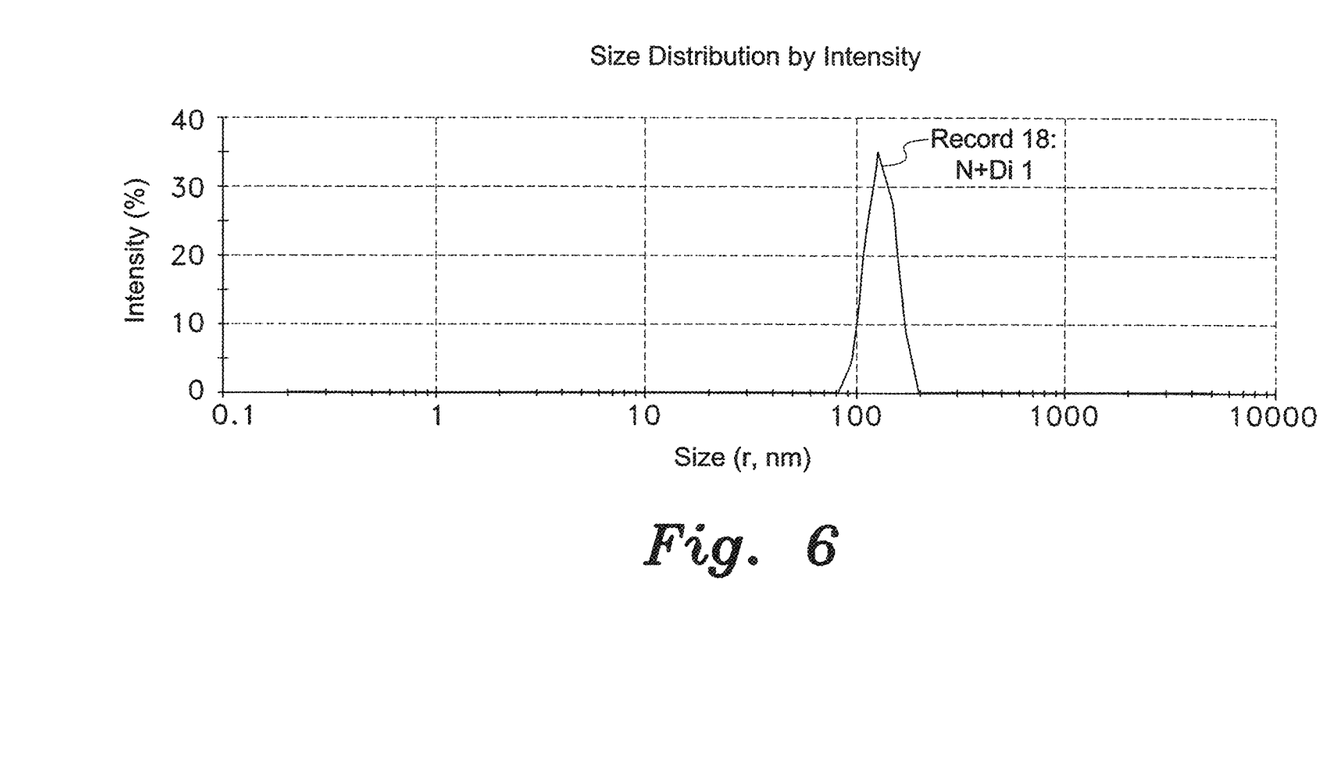
FIG. 6 is a graph showing the particle size distribution by intensity (Zetasizer) of the dichloromethane-naringenin nanoparticles.

About 100 mg of Naringenin powder was dissolved in about 20-50 ml dichloromethane. The naringenin-dichloromethane solution was sprayed into about 50-100 mL boiling water dropwise with a flow rate of 0.2 mL/min in 5 min under ultrasonic conditions, with an ultrasonic power of 100 W and a frequency of 30-60 kHz for 20-30 min. The solution was stirred for 15-30 min at 30-50° C. to obtain dichloromethane-naringenin nanoparticles. FIGS. 5A and 5B show the TEM images of the dichloromethane-naringenin nanoparticles as being clustered or rod shaped. FIG. 6 shows the dichloromethane-naringenin particle size distribution by intensity (zetasizer) of the dichloromethane naringenin nanoparticles, indicating the average particle size to be about 150 nm.

EXAMPLE 4

Synthesis of Naringenin Nanoparticles in Chloroform

Figure 7A:
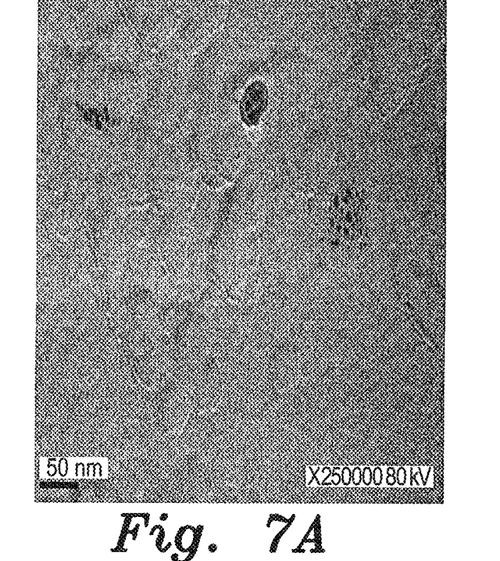
FIG. 7A-7B show the TEM images of the chloroform-naringenin nanoparticles.
Figure 7B:
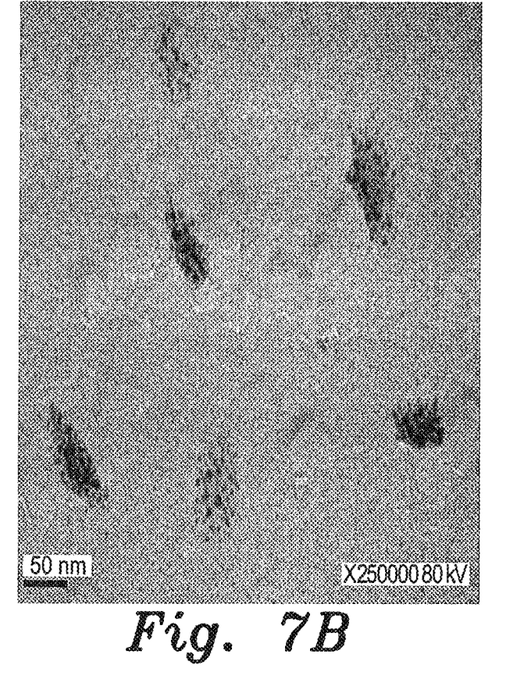
Figure 8:
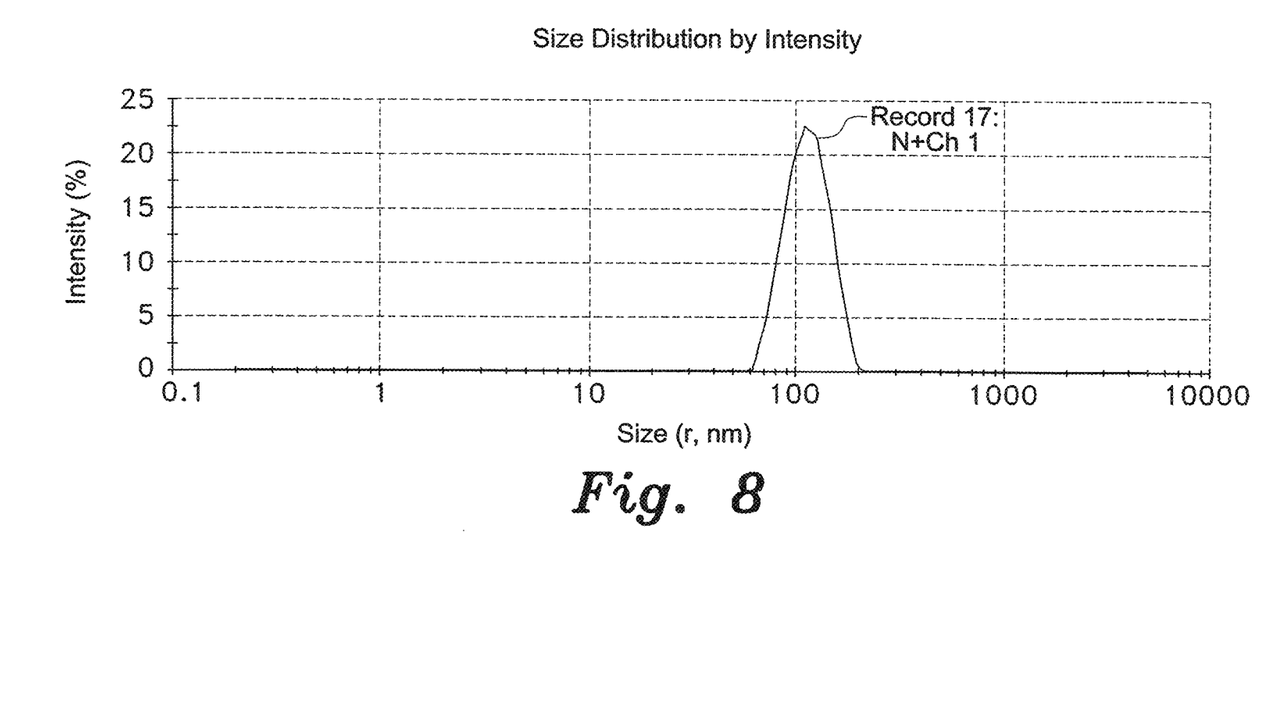
FIG. 8 is a graph showing the particle size distribution by intensity (Zetasizer) of the chloroform-naringenin nanoparticles.

About 100 mg of naringenin powder was dissolved in about 20-50 ml chloroform. The naringenin-chloroform solution was sprayed into about 50-100 mL boiling water dropwise with a flow rate of 0.2 mL/min in 5 min under ultrasonic conditions, with an ultrasonic power of 100 W and a frequency of 30-60 kHz for 20-30 min. The solution was stirred for 15-30 min at 30-50° C. until the chloroform-naringenin nanoparticles formed in solution. FIGS. 7A-7B show the TEM images of the chloroform-Naringenin nanoparticles that are clustered dots. FIG. 8: shows the naringenin particle size distribution by intensity of the chloroform naringenin nanoparticles indicating the average particle size to be about 120 nm.

EXAMPLE 5

Method of Treating Oxidative Stress Using Naringenin Particles in Nile Tilapia (*Oreochromis niloticus*)

Experimental design was as follows. Adult Nile tilapia, *Oreochromis niloticus* (n=120 fish), with an average length of 20±4 cm and weight of 150 g-200 g were procured from the local fish farm near Riyadh City. They were checked thoroughly for injury and disease conditions. After washing with 0.01% $KMnO_4$ solution for 15 min, they were divided into five groups each comprising 20 fish and kept in glass tanks (100 L capacity) with non-chlorinated tap water. Prior to the start of the experiment, the fish were acclimated to the food and laboratory conditions with 12 hr dark and 12 hr light cycles, pH range of 6 to 8 and temperature ranging from 20° C. to 24° C. for 15 days. The exposure period was 21 days. Through the entire experimental period the fish were fed commercial pelleted diet at 2% body weight.

The experimental groups were in replicates as follows. Group I was the negative control which contained dechlorinated tap water with no added $CdCl_2.H_2O$ and without any antioxidant treatment (designated "Control" in FIGS. 9-10). Group II was the positive control, which was exposed to a sub-lethal concentration of 5 ppm solution of waterborne $CdCl_2.H_2O$ (98% pure) (Kumar et al., 2009) (designated "Cd" in FIGS. 9-10). Group III was exposed to a sub-lethal concentration of 5 ppm solution of waterborne $CdCl_2.H_2O$ (98% pure) and treated with bulk naringenin extract (3 ppm) (designated "Cd+Bn" in FIGS. 9-10). Group IV was exposed to a sub-lethal concentration of 5 ppm solution of waterborne $CdCl_2.H_2O$ (98% pure) and treated with nanoparticles of naringenin (3 ppm) (designated "Cd+Nn" in FIGS. 9-10). Group V was exposed only to nanoparticles of naringenin (3 ppm) with no added $CdCl_2.H_2O$ (designated "Control" in FIGS. 9-10) (designated "Nn" in FIGS. 9-10). Group V was used as an additional control in the study to assess the effect of nano-formulation of naringenin on fish.

Naringenin both as bulk and nanoparticles was added in the tank water. The water, $CdCl_2$ and antioxidant treatments (bulk and nanoparticles of naringenin) of each experimental tank were changed after 48 hours. After the exposure period of 21 days the fish from each experimental group were dissected. The liver, kidneys, gills and muscle tissue were excised out for the biochemical analysis and determination of Cd accumulation. All tissues were stored at −80° C. till further analysis.

Cadmium concentration in tissues was determined as follows. Tissue samples of kidney, liver, gills and muscle (0.5 g each) were wet digested with nitric and perchloric acids (3:1) mixture. The concentration of Cd in digested tissue samples were analyzed in an atomic absorption spectrophotometer.

Biochemical analysis was performed as follows. A quantitation of MDA levels in the liver (lipid peroxides) was done by a high performance liquid chromatographic (HPLC) method. The activity of superoxide dismutase (SOD), catalase (CAT) in liver and kidney were also estimated using commercial ELISA kits. The levels of hepatic metalothionein levels (MT-2) and HSP70 in kidney were also assessed using commercial ELISA kits.

The results on the exposure study clearly suggest that an exposure of 21 days to Cd (5 ppm) in Nile tilapia, elicited toxicological effects which were mainly manifested as bioaccumulation of the metal in the tissues, oxidative stress and induction of stress proteins, MT-2 in the liver and HSP70 in the gills. The treatment with naringenin, both as bulk and nanonaringenin was efficacious in alleviating the Cd toxicity on Nile tilapia, which was evident from the end points evaluated;

The bioaccumulation of Cd was reduced in the liver and kidney on treatment. The modulation in the biomarkers of oxidative stress induced by Cd, such as MDA levels in the liver, CAT and SOD activity in liver and kidney were reversed on treatment. The induction of liver MT-2 levels and HSP70 in the gills was also reversed on treatment with naringenin.

The key findings clearly suggest a potent ameliorative effect of naringenin against Cd toxicity in fish, owing to its antioxidant and metal chelating properties. A broad assessment of the comparative efficacy of bulk naringenin and nanonaringenin showed that the effect on reducing the bioaccumulation in the liver and HSP70 was more profound in the group treated with nanonaringenin. The study also showed that the nano formulation of naringenin had no adverse effects on fish and retained the antioxidative and chelating properties of the bioflavonoid.

Figure 9:
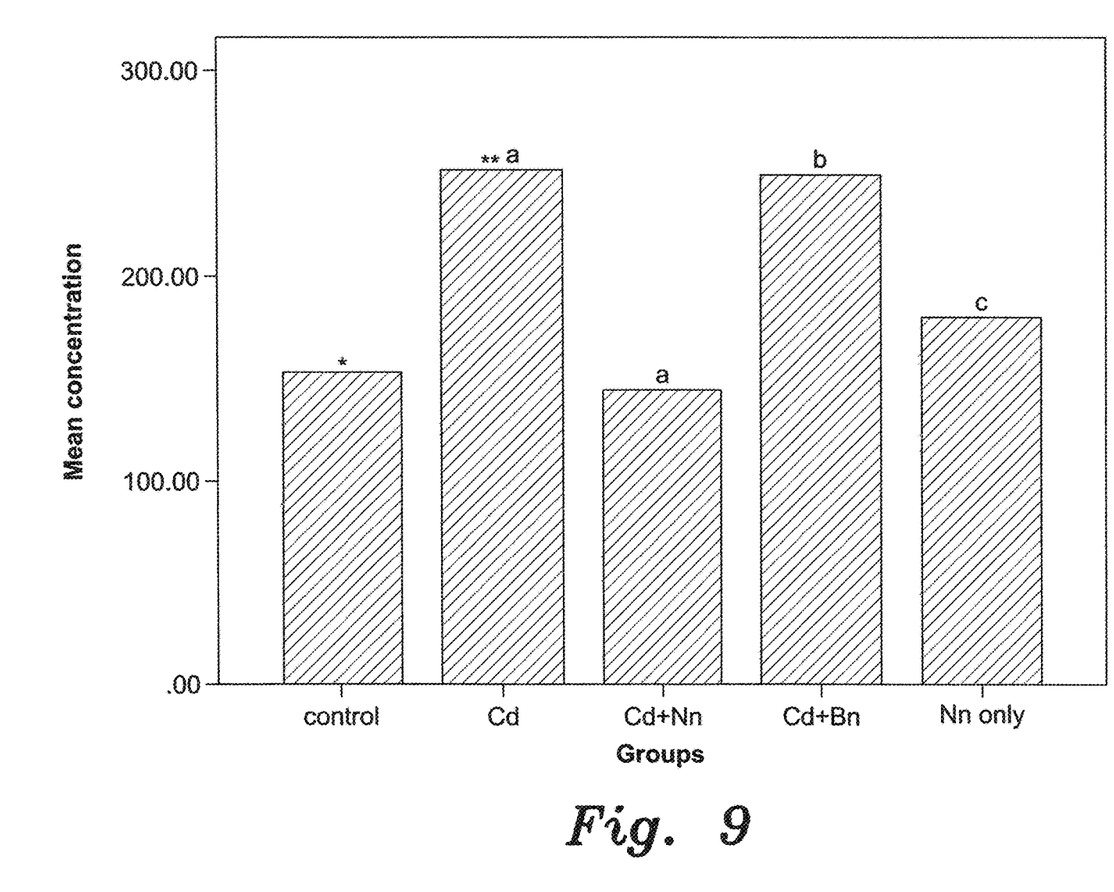
FIG. 9 is a graph showing the HSP70 levels in gills (pg/g) in liver of fish *Oreochromis niloticus* exposed to 5 ppm $CdCl_2 \cdot H_2O$ treated with bulk and nanonaringenin.

Heat shock protein (HSP70) in gills was determined as follows. The exposure to Cd (5 ppm) through a period of 21 days, significantly ($p \leq 0.05$) increased the HSP70 concentration (251.6600±19.36474 pg/g) in the gills of the fish exposed to Cd only in comparison to the control (152.8800±11.81554 pg/g). A significant ($p \leq 0.05$) reduction in the HSP70 concentration was observed in the Cd exposed group treated with nanonaringenin (Nn). However, treatment with bulk naringenin (Bn) did not show a significant effect on the HSP70 levels. The group exposed to nanonaringenin (Nn) only was comparable to the control (FIG. 9). FIG. 9 shows the HSP70 levels in gills (pg/g) of the fish groups. Different letters indicate significant difference between groups ($p \leq 0.05$).

Figure 10:
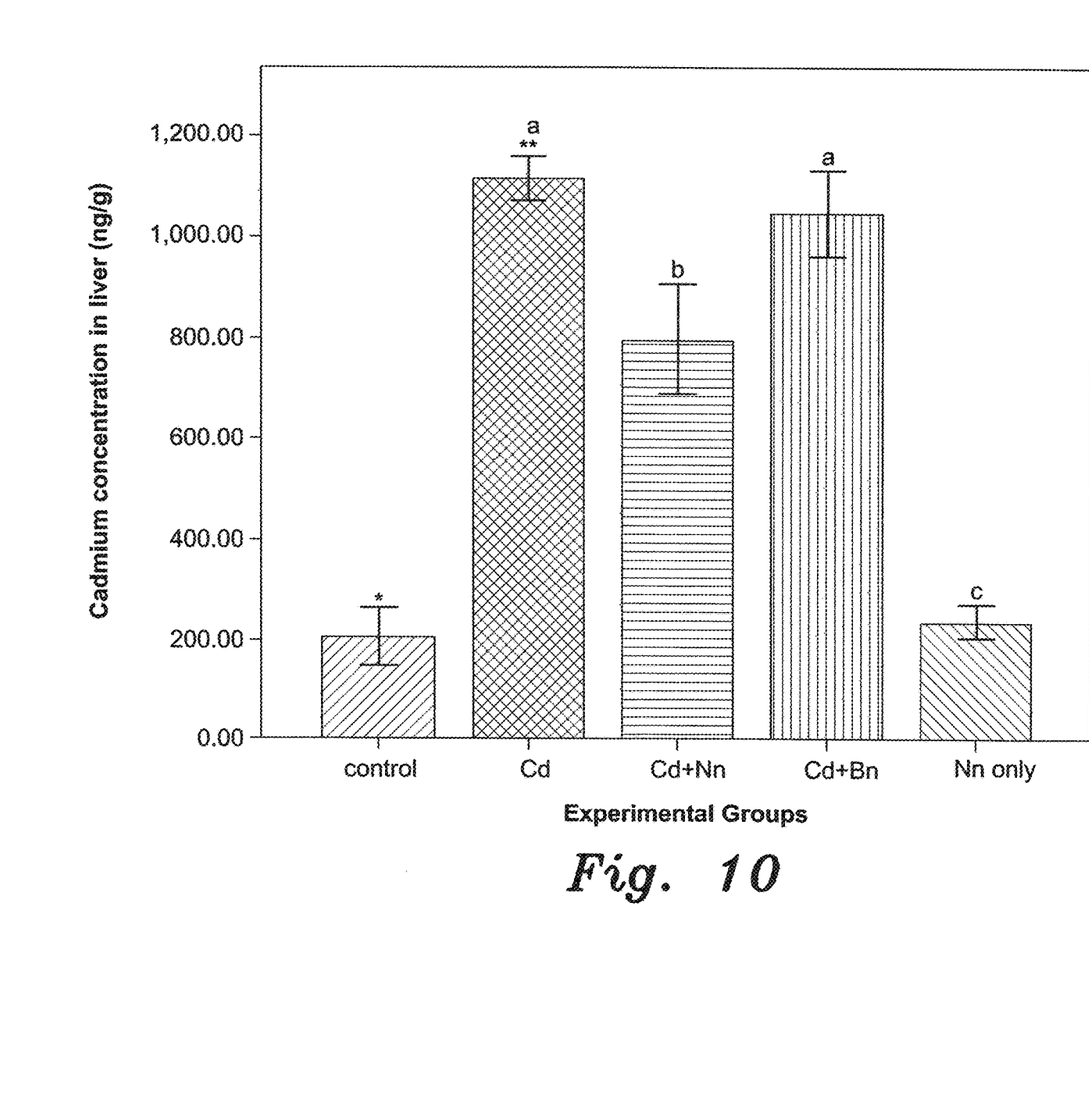
FIG. 10 is a graph showing the cadmium concentration (ng/g) in liver of fish *Oreochromis niloticus* exposed to 5 ppm $CdCl_2 \cdot H_2O$ treated with bulk and nanonaringenin.

Cadmium accumulation in liver was assessed as follows. After 21 days of exposure, the group exposed to Cd only (1113.3320±48.39 ng/g) showed a significant increase in the Cd concentration in the liver in comparison to the control group (205.4804±62.9 ng/g). Treatment with bulk naringenin (Cd+BNn) did not have any significant effect on the cadmium concentration in the liver, however treatment with nanonaringenin (Cd+NNn) significantly ($p \leq 0.05$) reduced the cadmium concentration in comparison to the non-treated Cd exposed group. The Cd concentration in the liver from the group exposed to nanonaringenin only (NNn), was comparable to the control group. FIG. 10 is a graph showing the cadmium concentration (ng/g) in the liver of the fish (*Oreochromis niloticus*) groups. Different letters indicate significant difference between groups ($p \leq 0.05$).

It is to be understood that the present invention is not limited to the embodiments described above but encompasses any and all embodiments within the scope of the following claims.

We claim:
1. A method of synthesizing naringenin nanoparticles, comprising:
dissolving naringenin in an organic solvent to form a solution;
adding the solution to boiling water, wherein the boiling water and the naringenin solution are both irradiated under ultrasonic conditions to form a mixture;
allowing the mixture to cool; and
stirring the mixture at a temperature of about 30° C. to about 50° C. to obtain naringenin nanoparticles.

2. The method of synthesizing naringenin nanoparticles according to claim 1, wherein the ultrasonic conditions include irradiation of the mixture with ultrasonic waves having a frequency of about 30 to about 60 kHz and with a power of about 100 watts.

3. The method of preparing naringenin nanoparticles according to claim 1, wherein the organic solvent is selected from the group consisting of at least one of methanol, ethanol, dichloromethane and chloroform.

4. The method of preparing naringenin nanoparticles according to claim 1, wherein the solution is added by spraying the solution dropwise into the boiling water at a rate of about 0.2 ml/minute.

5. The method of preparing naringenin nanoparticles according to claim 1, further comprising isolating the naringenin nanoparticles by at least one of centrifugation and filtration.

6. The method of synthesizing naringenin nanoparticles according to claim 1, wherein the naringenin nanoparticles have a mean diameter in the range of from about 50 nm to about 200 nm.

7. The method of synthesizing naringenin nanoparticles according to claim 1, wherein the naringenin nanoparticles have spherical, spheroidal, elongated spherical, rod-shaped, and/or faceted shapes.

8. A method of treating oxidative stress in an organism comprising administering an effective amount of naringenin nanoparticles to the organism, wherein the naringenin nanoparticles are synthesized by the method of claim 1.

9. The method of treating oxidative stress in an organism according to claim 8, wherein the organism is freshwater fish.

10. The method of treating oxidative stress in an organism according to claim 9, wherein the freshwater fish is Nile tilapia.

* * * * *